United States Patent [19]
Van Daele et al.

[11] Patent Number: 5,863,923
[45] Date of Patent: Jan. 26, 1999

[54] DIMETHYLBENZOFURAN AND DIMETHYLBENZOPYRAN DERIVATIVES AND THEIR USE AS 5-HT$_3$ ANTAGONISTS

[75] Inventors: Georges Henri Paul Van Daele, Turnhout; Jean-Paul René Marie André Bosmans, Edegem; Willy Joannes Carolus Van Laerhoven, Beerse, all of Belgium

[73] Assignee: Janssen Pharmaceutica N.V., Beerse, Belgium

[21] Appl. No.: 848,777

[22] Filed: May 1, 1997

Related U.S. Application Data

[60] Division of Ser. No. 416,914, filed as PCT/EP93/03206, Nov. 15, 1993, Pat. No. 5,674,868, which is a continuation-in-part of Ser. No. 979,013, Nov. 20, 1992.

[51] Int. Cl.$^6$ ........................ A61K 31/505; C07D 239/47
[52] U.S. Cl. ............................. 514/272; 544/321
[58] Field of Search ............... 514/272; 544/321

[56] References Cited

FOREIGN PATENT DOCUMENTS

| | | |
|---|---|---|
| A-0076530 | 4/1983 | European Pat. Off. . |
| A-0309043 | 3/1989 | European Pat. Off. . |
| A-0389037 | 9/1990 | European Pat. Off. . |
| A-0445862 | 9/1991 | European Pat. Off. . |

Primary Examiner—Yogendra N. Gupta
Attorney, Agent, or Firm—Ellen Ciambrone Coletti

[57] ABSTRACT

Method of treating 5-HT$_3$-mediated disorders, which comprises systemic administration of an effective amount of a compound of formula (I)

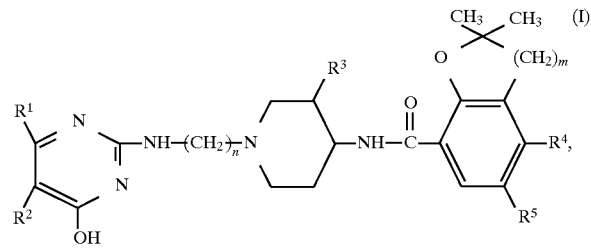

the pharmaceutically acceptable acid addition salt forms and the stereochemically isomeric forms thereof, wherein $R^1$ and $R^2$ represent hydrogen, or $R^1$ and $R^2$ taken together form a bivalent radical of formula —CH=CH—CH=CH— (a), —CH=C(Cl)—CH=CH— (b) or —CH=CH—C(Cl)=CH— (c); n represents 2, 3 or 4; $R^3$ represents hydrogen or methoxy; m represents 1 or 2; $R^4$ represents hydrogen, amino or $C_{1-3}$-alkylcarbonylamino; and $R^5$ represents hydrogen or halo; novel compounds; compositions; processes for preparing novel compounds and intermediates.

8 Claims, No Drawings

DIMETHYLBENZOFURAN AND DIMETHYLBENZOPYRAN DERIVATIVES AND THEIR USE AS 5-HT₃ ANTAGONISTS

CROSS-REFERENCE TO RELATED APPLICATIONS

This application is a divisional of application Ser. No. 08/416,914, filed on Jun. 16, 1995, now U.S. Pat. No. 5,674,868, which in turn was the national stage of PCT Application Ser. No. PCT/EP 93/03206, filed Nov. 15, 1993, which claims priority as a continuation-in-part from U.S. application Ser. No. 07/979,013, filed on Nov. 20, 1992.

BACKGROUND OF THE INVENTION

EP-0,389,037, published on Sep. 26, 1990 discloses N-(3-hydroxy-4-piperidinyl)(dihydrobenzofuran, dihydro-2H-benzopyran or dihydrobenzodioxin) carboxamide derivatives and EP-0,445,862, published on Sep. 11, 1991 discloses N-(4-piperidinyl)(dihydrobenzofuran or dihydrobenzo-2H-benzopyran)carboxamide derivatives. Both applications disclose gastrointestinal motility stimulating properties for said compounds. The dimethyl-dihydrobenzofuran and dimethyl-dihydro-2H-benzo-pyran derivatives of the present invention show 5-HT$_3$-antagonism.

DESCRIPTION OF THE INVENTION

The present invention is concerned with a method of treating warm-blooded animals suffering from 5-HT$_3$ mediated disorders such as anxiety, psychosis, depression, schizophrenia, cognitive disorders, drug abuse, migraine, emesis, irritable bowel syndrome and related disorders, which comprises the systemic administration to said warm-blooded animals of an effective 5-HT$_3$ antagonistic amount of a compound of formula

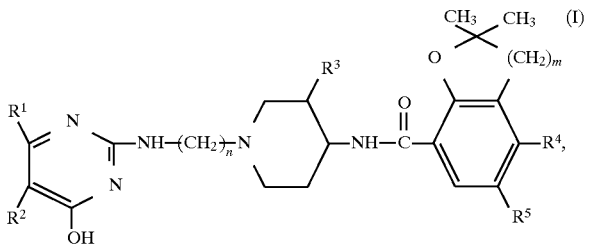

a pharmaceutically acceptable acid addition salt form or a stereochemically isomeric form thereof, wherein $R^1$ and $R^2$ represent hydrogen, or $R^1$ and $R^2$ taken together form a bivalent radical of formula
—CH=CH—CH=CH— (a),
—CH=C(Cl)—CH=CH— (b) or
—CH=CH—C(Cl)=CH— (c);

n represents 2, 3 or 4;

$R^3$ represents hydrogen or methoxy;

m represents 1 or 2;

$R^4$ represents hydrogen, amino or $C_{1-3}$alkylcarbonylamino; and $R^5$ represents hydrogen or halo.

The present invention is also concerned with the use of the compounds of formula (I), the pharmaceutically acceptable acid addition salts and the stereochemically isomeric forms thereof for the manufacture of a medicament for treating 5-HT$_3$ mediated disorders such as anxiety, psychosis, depression, schizophrenia, cognitive disorders, drug abuse, migraine, emesis, irritable bowel syndrome and related disorders.

In the foregoing definitions and hereinafter the term halo defines fluoro, chloro, bromo and iodo, preferably chloro; $C_{1-4}$alkyl defines straight and branch chained saturated hydrocarbon radicals having from 1 to 4 carbon atoms such as methyl, ethyl, propyl, 1-methylethyl, butyl, 1-methylpropyl, 2-methylpropyl and 1,1-dimethylethyl, preferably methyl. $C_{1-6}$alkyl defines $C_{1-4}$alkyl and the higher homologues thereof such as, for example, pentyl and hexyl. $C_{1-3}$alkylcarbonyl defines straight and branch chained acyl radicals such as methylcarbonyl, ethylcarbonyl, propylcarbonyl, preferably methylcarbonyl.

The term pharmaceutically acceptable acid addition salt as used hereinbefore defines the non-toxic, therapeutically active acid addition salt forms which the compounds of formula (I) may form. The compounds of formula (I), having basic properties, may be converted into the corresponding therapeutically active, non-toxic acid addition salt forms by treating the free base form with a suitable amount of an appropriate acid following conventional procedures. Examples of appropriate acids are inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, cyclohexane-sulfamic, 2-hydroxybenzoic, 4-amino-2-hydroxybenzoic and the like acids. The term pharmaceutically acceptable addition salts also comprises the solvates which the compounds of formula (I) may form such as alcoholates and in particular hydrates.

The compounds of formula (I) may also exist in their tautomeric form. Said form although not explicitly indicated hereinabove is intended to be included within the scope of the present invention.

The term stereochemically isomeric forms as used hereinbefore defines the different isomeric forms which the compounds of formula (I) may possess. Unless otherwise mentioned or indicated, the chemical designation of compounds denotes the mixture of all possible stereochemically isomeric forms, said mixtures containing all diastereomers, and/or enantiomers of the basic molelular structure. All stereochemically isomeric forms of the compounds of formula (I) both in pure form or in admixture with each other are intended to be embraced within the scope of the present invention.

Hereinafter the term 'enantiomerically pure' concerns compounds having an enantiomeric excess of at least 94% (i.e. minimum 97% of one enantiomer and maximum 3% of the other enantiomer) up to an enantiomeric excess of 100% (i.e. 100% of one enantiomer and none of the other), in particular compounds having an enantiomeric excess of 96% up to 100% more in particular having an enantiomeric excess of 98% up to 100%. The term "enantiomerically enriched" concerns compounds having an enantiomeric excess ranging from more than 0% up to about 94%. The terms "diastereomerically enriched" and "diastereomerically pure" as used hereinafter should be understood in a similar way, but then having regard to the diastereomeric excess of the mixture in question.

Interesting compounds for use as 5-HT$_3$ antagonists are those compounds of formula (I) wherein $R^5$ is halo, preferably chloro.

Also interesting compounds for use as 5-HT$_3$ antagonists are those compounds of formula (I) wherein $R^4$ represents hydrogen or amino.

More interesting compounds for use as 5-HT$_3$ antagonists are those compounds of formula (I) wherein $R^1$ and $R^2$ represent hydrogen;

n represents 2 or 3;

$R^3$ represents methoxy and has the cis-configuration;

m represents 1;

$R^4$ represents amino; and $R^5$ represents halo.

Particularly interesting compounds for use as 5-HT$_3$ antagonists are those interesting compounds of formula (I), wherein $R^3$ is methoxy having the cis-configuration, that are laevo-rotatory.

Preferred compounds are (-)-cis-4-amino-5-chloro-2,3-dihydro-N-[1-[3-[(3,4-dihydro-4-oxo-2-pyrimidinyl)amino]propyl]-3-methoxy-4-piperidinyl]-2,2-di-methyl-7-benzofurancarboxamide and (-)-cis-4-amino-5-chloro-N-[1-[2-[(3,4-dihydro-4-oxo-2-pyrimidinyl)amino]ethyl]-2,3-dihydro-3-methoxy-4-piperidinyl]-2,2-dimethyl-7-benzofurancarboxamide, and the pharmaceutically acceptable acid addition salts thereof.

The compounds of formula (I), wherein $R^3$ is methoxy and has the cis-configuration are represented by formula (I-a). Hereinafter the intermediates wherein $R^3$ is methoxy and where possible has the cis-configuration will be designated by appending the suffix -a to their numerical reference.

An additional feature of the present invention comprises the fact that the laevo-rotatory enantiomers of the compounds of formula (I) wherein $R^3$ represents methoxy and has the cis-configuration, i.e. the laevorotatory enantiomers of the compounds of formula (I-a), are deemed novel.

The compounds of formula (I) can generally be prepared following art-known procedures such as described in EP-0,389,037 and alternative processes known in the art. Some intermediates of formula (II), (III), (IV), (V), (VI), (VII), (IX), (X) and (XIII) are described in EP-0,389,037, EP-0,445,862 and EP-0,076,350. Some methods for preparing compounds of formula (I), especially compounds of formula (I-a), and novel intermediates will be described hereinunder.

In the following preparations, the reaction products may be isolated from the reaction mixture and, if necessary, further purified according to methodologies generally known in the art such as, for example, extraction, distillation, crystallization, trituration and chromatography.

In order to simplify the structural representations of the compounds of formula (1) and certain starting materials and intermediates thereof, the radical

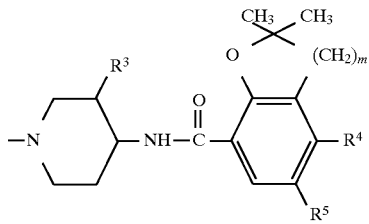

will hereafter be represented by the symbol D and the radical

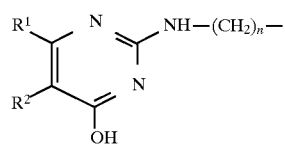

will hereafter be represented by L.

The compounds of formula (I) may be prepared by N-alkylating a piperidine of formula (II) with an intermediate of formula (III).

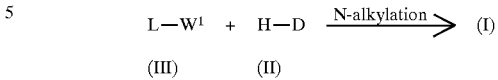

$W^1$ as described in the reaction of (III) with (II) and in the following reaction schemes is an appropriate leaving group such as, for example, halo, e.g. chloro, bromo or iodo, or a sulfonyloxy group, e.g. methanesulfonyloxy, 4-methylbenzenesulfonyloxy and the like leaving groups. The N-alkylation reaction of (II) with (III) is conveniently conducted following art-known alkylation procedures.

The compounds of formula (I) may also be prepared by the N-acylation of an amine of formula (IV) with a carboxylic acid of formula (V) or a functional derivative thereof, such as an acylhalide, a symmetrical or mixed anhydride or an ester, preferably an activated ester, following art-known procedures.

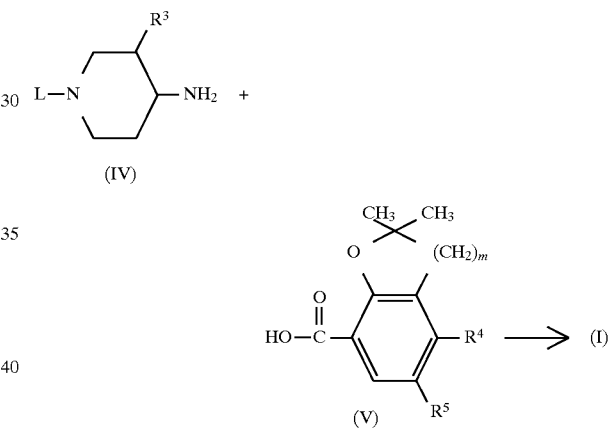

It may be expedient to protect amino or hydroxy groups during the course of the reaction to avoid undesired side reactions. Suitable protecting groups comprise readily removable groups such as $C_{1-4}$alkylcarbonyl, $C_{1-4}$alkyloxycarbonyl, phenylmethyl, tertiary butyl and the like protective groups.

The compounds of formula (I) may also be prepared by N-alkylating an intermediate of formula (VII) with an alkylating reagent of formula (VI), wherein $R^6$ is hydrogen or $C_{1-6}$alkyl and $W^2$ is an appropriate leaving group such as, for example, halo, e.g. chloro, bromo or iodo; a sulfonyloxy group, e.g. methanesulfonyloxy, 4-methyl-benzenesulfonyloxy; $C_{1-6}$alkyloxy, e.g. methoxy, ethoxy; $C_{1-6}$alkylthio, e.g. methylthio, ethylthio. When $R^6$ is $C_{1-6}$alkyl an intermediate of formula (VIII) is formed, which may subsequently be transformed into the final compounds by cleaving the protective etherfunction. Said cleavage may be carried out by treating the intermediate of formula (VIII) with an acid, such as, for example, a hydrohalic acid, e.g. hydrochloric acid.

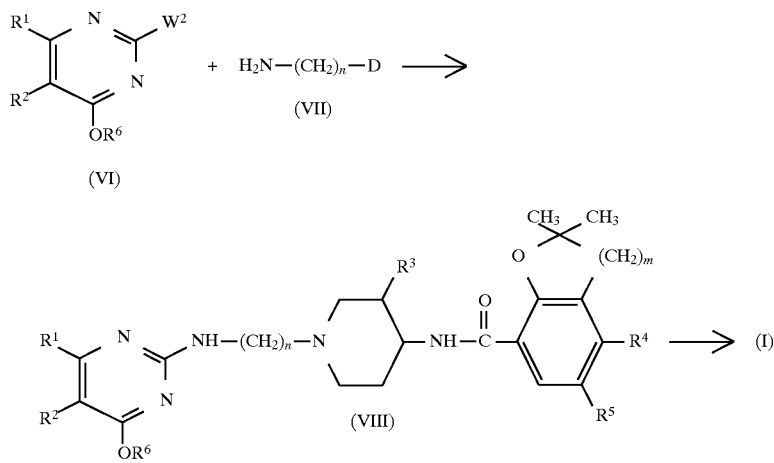

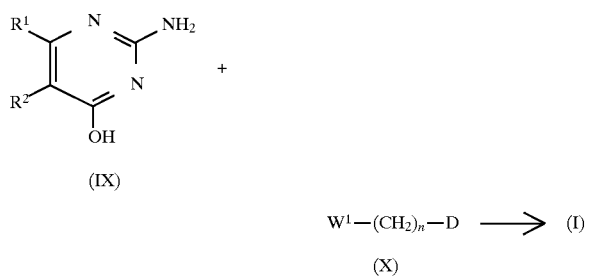

The compounds of formula (I) can alternatively be prepared by N-alkylating an 2-amino-pyridine of formula (IX) with an intermediate of formula (X).

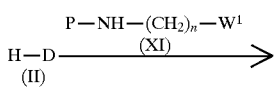

The alkylation reactions of (VI) with (VII) and (IX) with (X) may be carried out according to art-known procedures, e.g. by stirring and optionally heating the reactants without solvent or in admixture with an inert organic solvent such as, for example an alcohol, e.g. 2-propanol, butanol, a dipolar aprotic solvent, e.g. acetonitrile optionally in the presence of an appropriate base, e.g. potassium carbonate.

The compounds of formula (I) may also be converted into each other following art-known group-transformation reactions.

Aminogroups may be transformed in $C_{1-3}$alkylcarbonylamino by art-known N-acylation reactions and conversely $C_{1-3}$alkylcarbonylamino groups may be transformed in amino groups using art-known hydrolysis reactions.

Compounds of formula (I), wherein $R^5$ is hydrogen may be transformed in the corresponding compounds wherein $R^5$ is halogen, using art-known halogenation techniques.

The intermediates of formula (VII) may be prepared by N-alkylating an intermediate of formula (II) with a reagent of formula (XI) and subsequently removing the protective group P in the thus obtained intermediate (XIII) following art-known reaction procedures.

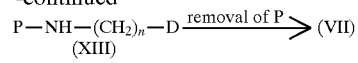

In (XI), (XIII) and the other intermediates containing the group P in the following schemes, P represents a suitable protective group which is readily removable by, for example, hydrogenolysis or hydrolysis. Preferred protective groups are, for example, $C_{1-4}$alkylcarbonyl, e.g. methylcarbonyl, ethylcarbonyl; $C_{1-4}$alkoxycarbonyl, e.g. ethoxycarbonyl, 1,1'-dimethylethyloxycarbonyl; trihalomethylcarbonyl, e.g. trifluoro-methylcarbonyl; diphenylmethyl; triphenylmethyl or arylmethyl, wherein aryl is phenyl optionally substituted with up to two substituents selected from $C_{1-4}$alkyloxy or halo.

The intermediates of formula (II) may be derived from an appropriately substituted piperidine of formula (XIV) with an intermediate acid of formula (V) or a functional derivative thereof, following art-known amide forming procedures, and subsequently removing the protective group $P^1$, following art-known procedures. $P^1$ represents a readily removable protective group and has the same meaning as the group P hereinabove.

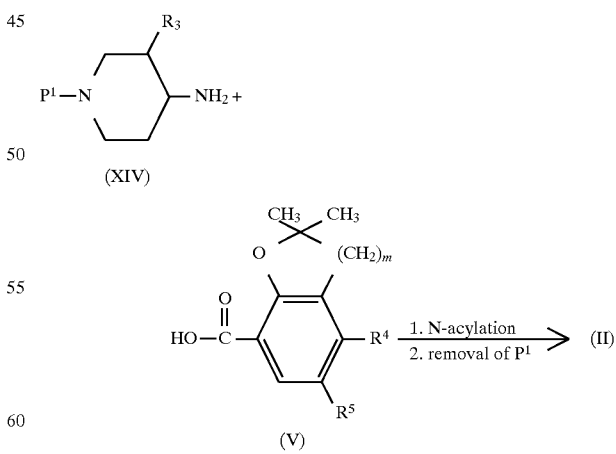

The intermediates of formula (XIV), wherein $R^3$ is methoxy and has the cis-configuration, i.e. the 3-methoxy-4-aminopiperidines of formula (XIV-a), may be obtained, for example, by catalytic hydrogenation of an imine of formula (XVI-a) and subsequently transforming the secondary amine of formula (XV-a) into the 3-methoxy- 4-aminopiperidines of formula (XIV-a) by hydrogenolysis. The imines of formula (XVI-a) may be prepared following art-known imine formation procedures starting from a 3-methoxy-4-oxo-piperidine of formula (XVII-a) and an amine of formula (XVIII).

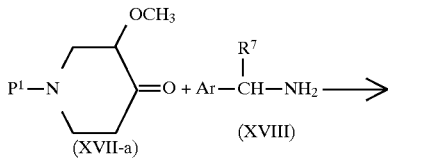

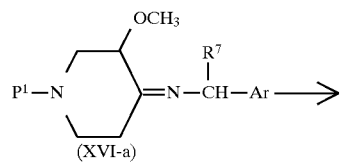

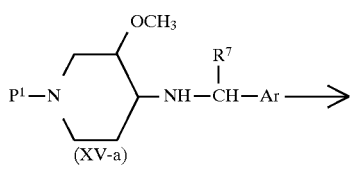

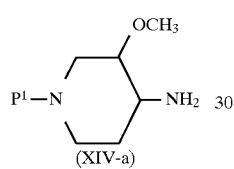

In the intermediates of formula (XVIII), (XVI-a) and (XV-a), $R^7$ is hydrogen, $C_{1-6}$alkyl or hydroxy$C_{1-6}$alkyl and Ar is phenyl optionally substituted with halo, $C_{1-6}$alkyl, $C_{1-6}$alkyloxy; or naphthyl optionally substituted with halo, $C_{1-6}$alkyl, $C_{1-6}$alkyloxy.

The reactionsequence starting from an intermediate of formula (XVII-a) up to an intermediate of formula (XIV-a) may also be performed as a one-pot procedure.

Enantiomerically enriched or enantiomerically pure intermediates of formula (XV-a) and (XIV-a) may be prepared according to one of the following methods.

The starting racemic 3-methoxy-4-oxo-piperidine of formula (XVII-a) or the corresponding ketal such as, for example, a di$C_{1-6}$alkylketal, e.g. 4,4-diethoxy-3-methoxypiperidine, may be separated into its enantiomers and further converted into an enantiomerically pure cis-3-methoxy-4-aminopiperidine of formula (XIV-a) as described hereinabove. Said separation in enantiomers can be performed, for instance, by column chromatography using a chiral stationary phase, e.g. Chiracell OD.

Alternatively, the intermediate imine of formula (XVI-a) can be prepared using one of the enantiomers of a chiral amine of formula (XVIII), wherein $R^7$ is defined as hereinabove but other than hydrogen, said amines being represented by (XVIII-b), e.g. (-)-(R)-α-aminobenzene-ethanol or (+)-S-α-aminobenzeneethanol, which after hydrogenation yields diastereomeric amines of formula (XV-a), which may be conveniently separated by physical separation methods such as selective crystallization or chromatographic techniques. Hydrogenolysis of the arylmethylgroup (Ar—CH($R^7$)-) from the respective diastereomeric amines of formula (XV-a) yields the respective enantiomeric 3-methoxy-4-aminopiperidines of formula (XIV-a).

Yet another way of obtaining enantiomerically pure 3-methoxy-4-aminopiperidines of formula (XIV-a) was found during the optimization of the above reaction sequence. When one reacts a racemic ketone such as a 3-methoxy-4-oxo-piperidine of formula (XVII-a) with an enantiomerically pure chiral amine of formula (XVIII-b), e.g. (-)-(S)-α-methylbenzylamine, and subsequently hydrogenates the thus formed imine of formula (XVI-a), one would expect a ratio of diastereomeric amines of formula (XV-a) of approximately 1:1 . Unexpectedly, however, it was found that after the above reaction sequence said diastereomeric ratio differs substantially from the ratio 1:1. In other words, the amines of formula (XV-a) were diastereomerically enriched or even diastereomerically pure. Hence, in the course of this reaction sequence one diastereomer is converted into the other by configurational inversion of the stereocenter bearing the methoxygroup.

Thus, a novel and inventive way to obtain novel enantiomerically enriched or enantiomerically pure 3-methoxy-4-aminopiperidines of formula (XIV-a) and more in general intermediates of formula (XIX-a) was found following the procedure described in more detail hereinunder.

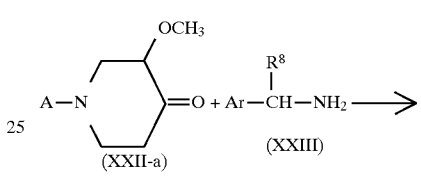

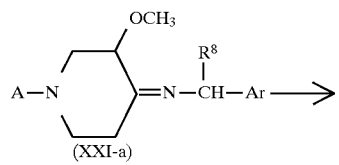

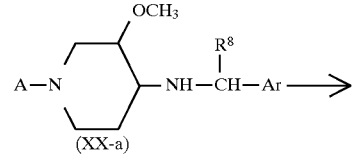

In (XIX-a), (XX-a), (XXI-a) and (XXII-a) the radical A represents hydrogen, —(CH$_2$)$_n$—NH$_2$, —(CH$_2$)$_n$—NH—P, $P^1$ or L, wherein n, P, $P^1$ and L are as defined hereinabove. A racemic mixture of 3-methoxy-4-oxo-piperidine of formula (XXII-a) may be reacted with one enantiomer of a chiral amine of formula (XXIII), wherein $R^8$ is $C_{1-6}$alkyl or hydroxy$C_{1-6}$alkyl, Ar is phenyl optionally substituted with halo, $C_{1-6}$alkyl, $C_{1-6}$alkyloxy; or naphthyl optionally substituted with halo, $C_{1-6}$alkyl, $C_{1-6}$alkyloxy; yielding a diastereomeric mixture of the intermediate imine of formula (XXI-a). Said reaction may be carried out using art-known imine-formation procedures, such as, for instance, stirring the reactants at reflux temperature in a reaction-inert solvent such as, for example, an aromatic hydrocarbon, e.g. methylbenzene, using a Dean-Stark apparatus.

The imine of formula (XXI-a) may be isolated and, if necessary, purified, for instance by column chromatography, distillation or cystallization. Subsequently the imine may be hydrogenated by stirring the imine under hydrogen atmosphere in a suitable solvent such as, for example, an alcohol, e.g. methanol or ethanol; an ether, e.g. tetrahydrofuran or 2,2'-oxybispropane; an ester, e.g. ethylacetate; an aromatic hydrocarbon, e.g. methylbenzene; in the presence of appropriate catalysts, e.g. palladium-on-charcoal, platinum-on-charcoal, rhodium-on carbon and the like, yielding a diastereomerically enriched or diastereochemically pure amine of formula (XX-a).

Alternatively, the intermediate imine of formula (XXI-a) is not isolated. In this case a racemic mixture of a 3-methoxy-4-oxo-piperidine of formula (XXII-a) is reacted with one of the enantiomers of a chiral amine of formula (XXIII) under hydrogenation conditions, yielding diastereomerically enriched or diastereomerically pure intermediate amines of formula (XX-a). Said reaction is performed in analogous reaction conditions as described hereinabove. However in this case, the reaction preferably is performed in admixture with an acid, such as, acetic acid, oxalic acid, chloroacetic acid, 2-hydroxy-1,2,3-propanetricarboxylic acid, and in particular (-) [S-(R*,R*)]-2,3-dihydroxybutanedioic acid, especially when the solvent is an alcohol.

In the amines of formula (XXIII), $R^8$ is suitably hydroxymethyl, methyl or ethyl, especially methyl and Ar is preferably an unsubstituted phenyl or naphthyl, especially phenyl. Preferred amines of formula (XXIII) are the enantiomers of α-methylbenzyl-amine, i.e. (-)-(S)-α-methylbenzylamine or (+)-(R)-(α-methylbenzylamine.

Sometimes, during the hydrogenation reaction a small amount of trans-3-methoxy-4-aminoderivative can be formed, which may be removed by crystallization or chromatography.

A preferred way of preparing a diastereomerically enriched or pure amine of formula (XX-a) is first preparing an imine of formula (XXI-a) with one enantiomer of α-methyl-benzylamine and subsequently hydrogenating the imine of formula (XXI-a) by stirring it in methylbenzene under a hydrogen atmosphere using a rhodium catalyst.

In order to avoid the undesired further hydrogenation of certain functional groups in the reactants and the reaction products, it may be advantageous to add an appropriate catalyst-poison to the reaction mixture, e.g. thiophene, quinoline-sulphur and the like. Higher pressures and/or temperatures may enhance the reaction rate.

The resulting intermediate of formula (XX-a) has a diastereomeric ratio, that differs very much from the 1:1 ratio. In other words, the intermediate of formula (XX-a) is diastereomerically enriched or diastereomerically pure. The respective diastereomeric forms may then, if necessary, be further separated using conventional physical methods such as chromatography or fractional crystallization optionally after salt formation. The thus obtained diastereomerically pure amines of formula (XX-a) may then be further hydrogenolyzed, removing the chiral auxiliary group Ar—CH($R^8$)—, yielding enantiomerically pure 3-methoxy-4-aminopiperidines of formula (XIX-a).

It is noteworthy that the configuration of the stereocenter bearing the methoxygroup is determined by the configuration of the enantiomerically pure amine of formula (XVIII) that is used. Hence, either configuration of said stereocenter can be obtained by selection of one or the other enantiomer of the amine of formula (XXIII). It may further be noted that the choice of the acid used during the hydrogenation of the imine, can also influence up to a certain degree the diastereomeric ratio of the amines of formula (XIX-a). The choice of catalyst can also influence up to a certain degree the amount of trans-4-amino-3-methoxy derivative that is formed.

The diastereomerically enriched or diastereomerically pure intermediates of formula (XX-a) and the enantiomerically enriched or enantiomerically pure intermediates of formula (XIX-a) and the pharmaceutically acceptable acid addition salts thereof are deemed novel. Also the enantiomerically enriched or enantiomerically pure intermediates of formula (II-a), (IV-a), (VII-a), (X-a), (XIII-a), (XIV-a) and the pharmaceutically acceptable acid addition salts are also deemed novel. Said intermediates may be prepared as described hereinabove starting from enantiomerically enriched or enantiomerically pure intermediates of formula (XIV-a).

In this way and starting from enantiomerically enriched or enantiomerically pure intermediates described hereinabove a novel and inventive way to prepare enantiomerically enriched or enantiomerically pure compounds of formula (I-a), especially, the laevo-rotatory enantiomers of the compounds of formula (I-a) is provided.

It is evident that the cis and trans diastereomeric racemates of the compounds of formula (I), (I-a), or any of the other intermediates may also be resolved into their optical isomers, cis(+), cis(-), trans(+) and trans(-) by the application of art-known methodologies. Diastereoisomers may be separated by physical separation methods such as selective crystallization and chromatographic techniques, e.g. counter current distribution, and enantiomers may be separated from each other by the selective crystallization of their diastereomeric salts with enantiomerically pure acids or their enantiomerically pure derivatives.

The compounds of formula (I), the pharmaceutically acceptable salts and stereoisomeric forms are 5-$HT_3$-receptor antagonists, as demonstrated by the fact that they have been found active, for example, in antagonising the von Bezold-Jarish chemoreflex evoked by serotonin in rats (Pharmacology and Toxicology, 70, Supp II, 17–22 (1992)). This test is described hereinafter as example 10.

The compounds of formula (I), especially the compounds of formula (I-a), are active during a long period of time. Moreover, the present compounds of formula (I), especially the compounds of formula (I-a), show a high degree of cardiovascular safety.

In view of their 5-$HT_3$-antagonistic activity the subject compounds may be formulated into various pharmaceutical forms for administration purposes. To prepare these pharmaceutical compositions, an effective amount of a particular compound, in base or acid addition salt form, as the active ingredient is intimately mixed with a pharmaceutically acceptable carrier. Said carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of the compounds of formula (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their $5$-$HT_3$-antagonising activity the compounds of formula (I) and especially the novel compounds of formula (I-a) are useful in the treatment of $5$-$HT_3$-mediated disorders such as anxiety, psychosis, depression (Arzneim. Forsch., 42(1), 239–246 (1992)), schizophrenia, cognitive disorders, e.g. memory impairment (Arzneim. Forsch., 42(1), 246–249 (1992)), drug abuse, migraine, emesis, e.g. cytotoxic drug and radiation induced emesis (Drugs 42(4), 551–568 (1991)), irritable bowel syndrome, especially diarrheapredominant irritable bowel syndrome, and related disorders. Consequently, the present invention provides a method of treating warm-blooded animals suffering from $5$-$HT_3$-mediated diseases such as anxiety, psychosis, depression, schizophrenia, cognitive disorders, e.g. memory impairment, drug abuse, migraine, emesis, e.g. cytotoxic drug and radiation induced emesis, irritable bowel syndrome, especially diarrheapredominant irritable bowel syndrome, and related disorders. Said method comprises the systemic administration of an effective $5$-$HT_3$-antagonistic amount of a compound of formula (I), a pharmaceutically acceptable acid addition salt or a stereoisomeric form thereof, to warm-blooded animals.

The present compounds of formula (I) are useful for the manufacture of a medicament for treating $5$-$HT_3$ mediated diseases. The novel compounds of formula (I-a) are useful as a medicine.

In general it is contemplated that an effective amount would be from about 0.001 mg/kg to about 50 mg/kg body weight, preferably from about 0.02 mg/kg to about 5 mg/kg body weight. A method of treatment may also include administering the active ingredient on a regimen of between two or four intakes per day.

EXPERIMENTAL PART

A. Preparation of the intermediates

EXAMPLE 1 a) 3,4,4-trimethoxy-1-(phenylmethyl)piperidine (0.676 mol) was purified by column chromatography over silica gel (eluent: $CH_2Cl_2/CH_3OH$ 98/2). The pure fractions were collected and the solvent was evaporated. This residue (mixture of enantiomers) was separated in it's enantiomers by column chromatography over a Chiracell OD column (eluent: hexanes/2-propanol 98.5/1.5). The fraction, corresponding to a first chromatographic peak, was collected and the solvent was evaporated. A sample was purified by distillation (bp at 0.5 mmHg: 120° C.), yielding: 56 g of (-)-3,4,4-trimethoxy-1-(phenylmethyl)piperidine $[\alpha]_{20}^D=-54.00°$ (c=0.5% in methanol) (interm. 1).

The fraction, corresponding to a second chromatographic peak, was collected and the solvent was evaporated. A sample was purified by distillation (bp at 0.5 mmHg: 120° C.), yielding 64 g of (+)-3,4,4-trimethoxy-1-(phenylmethyl) piperidine; $[\alpha]_{20}^D=49.60°$ (c=0.5% in methanol) (interm. 2).

b) A mixture of intermediate (1) (0.21 mol) in methanol (600 ml) was hydrogenated at 50° C. with palladium-on-charcoal 10% (3g) as a catalyst. After uptake of $H_2$ (1 equiv), the catalyst was filtered off. Calcium oxide (0.63 mol) was added to the filtrate. The reaction mixture was stirred at room temperature. Ethyl chloroformate (0.63 mol) was added dropwise. The reaction mixture was stirred for 2 hours at 50° C. The reaction mixture was stirred overnight at room temperature. The solvent was evaporated. Methylbenzene was added to the residue. The suspension was filtered and the filtrate was evaporated. The residue was purified by distillation, yielding 32.6 g (63%) of (-)-ethyl 3,4,4-trimethoxy-1-piperidinecarboxylate; $[\alpha]_{20}^D=-39.40°$ (c=0.5% in methanol) (interm. 3).

c) A mixture of interm. (3) (0.132 mol), 4-methylbenzenesulfonic acid (0.6 g) in 2-propanone (180 ml) and water (30 ml) was stirred and refluxed for 18 hours. The reaction mixture was cooled and N,N-diethylethanamine (0.6 ml) was added. The solvent was evaporated (temperature was kept <40° C.). The residue was dissolved in $CH_2Cl_2$. This solution was washed twice with a saturated NaCl solution. The organic layer was separated, dried ($MgSO_4$), filtered and the solvent was evaporated. The residue was purified by distillation, yielding 19.2 g (-)-ethyl 3-methoxy-4-oxo-1-piperidine-carboxylate (72.3%); $[\alpha]_{20}^D=44.40°$ (c=0.5% in methanol) (interm. 4).

d) A mixture of intermediate (4) (0.095 mol) and benzenemethanamine (0.11 mol) in methanol (200 ml) was hydrogenated under atmospheric conditions with palladium on activated charcoal 10% (2 g) as a catalyst in the presence of 4% solution of thiophene in 2,2'-oxybispropane (2 ml). After uptake of hydrogen, the catalyst was filtered off and the filtrate was evaporated. The residue was dissolved in methanol (250 ml) and the resulting mixture was hydrogenated at 50° C. with palladium on activated charcoal 10% (2 g) as a catalyst. After uptake of hydrogen (1 equiv), the catalyst was filtered off and the filtrate was evaporated. The residue was purified by distillation (bp at 0.1 mm Hg: 85° C.), yielding 13.4 g (70%) ethyl (-)-cis-4-amino-3-methoxy-1-piperidinecarboxylate; $[\alpha]_{20}^D=78.9°$ (c=1% in methanol) (interm. 5).

In a similar manner but starting from intermediate (2) was also prepared: (+)-ethyl cis-4-amino-3-methoxy-1-piperidinecarboxylate; $[\alpha]_{20}^D=80.64°$ (c=0.6% in methanol) (interm. 6).

EXAMPLE 2 a) A mixture of ethyl 3-methoxy-4-oxo-1-piperidinecarboxylate (0.5 mol), (-)-(S)-α-methylbenzenemethanamine (0.53 mol), 4-methylbenzenesulfonic acid monohydrate (1.25 g) and methylbenzene (625 ml) was stirred and refluxed with a Dean-Stark apparatus for 3 hours. The reaction mixture was evaporated and distilled, yielding 121 g (79.5%) of (-)-ethyl [cis(S)]-3-methoxy-4-[(1-phenylethyl)imino]-1-piperidinecarboxylate (interm. 7).

b) A mixture of intermediate (7) (0.4 mol) and methylbenzene (750 ml) was hydrogenated at room temperature and atmospheric pressure with rhodium-on-carbon (5 g) as a catalyst. After uptake of hydrogen (1 eq.), the catalyst was filtered off and the filtrate was evaporated. The residue was dissolved in 4-methyl-2-pentanone and converted into the 4-methylbenzenesulfonic acid salt (1:1) with 4-methylbenzenesulfonic acid. monohydrate (1 eq.). The salt was filtered off and dried. This fraction was recrystallized twice from a mixture of 2,2'-oxybispropane/methanol (250 ml/180 ml). The precipitated product was filtered off and dried, yielding 61.7 g (32.5%) of (-)-ethyl [cis(S)]-3-methoxy-4-[(1-phenylethyl)amino]-1-piperidinecarboxylate 4-methylbenzene-sulfonate (1:1); $[\alpha]_{20}^D = -62.16°$ (c=1% in methanol) (interm. 8).

In a similar manner, but using (+)-(R)-α-methylbenzene methanamine was prepared: (+)-ethyl [cis, (R)]-3-methoxy-4-[(1-phenylethyl)amino]-1-piperidinecarboxylate 4-methylbenzenesulfonate (1:1); $[\alpha]_{20}^D = 62.79°$ (c=1% in methanol) (interm. 9).

EXAMPLE 3 a) A mixture of ethyl 3-methoxy-4-oxo-1-piperidinecarboxylate (0.2 mol), (-)-(S)-α-methylbenzenemethanamine (0.4 mol) and (-)-[S-(R*,R*)] 2,3-dihydroxybutanedioic acid (0.2 mol) in methanol (500 ml) was hydrogenated at room temperature and atmospheric pressure with palladium on activated charcoal 10% (2 g) as a catalyst, in the presence of a 4% solution of thiophene in 2,2'-oxybispropane (2 ml). After uptake of $H_2$ (1 eq.), the catalyst was filtered off and the filtrate was evaporated. The residue was partitioned between methylbenzene and $H_2O$/$NH_4OH$. The organic layer was separated, dried ($MgSO_4$), filtered and the solvent was evaporated. The residue was dissolved in 4-methyl-2-pentanone and converted into the 4-methylbenzenesulfonic acid salt (1:1) with 4-methylbenzenesulfonic acid. monohydrate (1 eq.). The salt was filtered off and dried. This fraction was recrystallized from 2,2'-oxybispropane/$CH_3OH$ (500 ml/100 ml). The mixture was stirred for 24 hours. The precipitate was filtered off and dried (vacuum; 50° C.), yielding 32 g of (-)-ethyl [cis,(S)]-3-methoxy-4-[(1-phenylethyl)amino]-1-piperidinecarboxylate 4-methylbenzenesulfonate (1:1); $[\alpha]_{20}^D = -61.6°$ (c=0.5% in methanol) (interm. 8).

In a similar manner, but using (+)-(R)-α-methylbenzene methanamine, was also prepared: (+)-ethyl [cis, (R)]-3-methoxy-4-[(1-phenylethyl)amino]-1-piperidinecarboxylate 4-methylbenzenesulfonate (1:1) (interm. 9).

b) Intermediate (8) (0.067 mol) was converted into the free base with aqueous ammonia. This mixture was extracted with methylbenzene. The organic layer was separated, dried ($MgSO_4$), filtered and the solvent was evaporated. The residual free base was dissolved in methanol (250 ml) and hydrogenated at room temperature and atmospheric pressure with palladium on activated charcoal 10% (2 g) as a catalyst. After uptake of $H_2$ (1 equiv), the catalyst was filtered off and the filtrate was evaporated. The residue was purified by distillation (boiling point at 0.1 mm Hg: 85° C.), yielding 9.9 g (79.2%) of ethyl (-)-cis-4-amino-3-methoxy-1-piperidinecarboxylate (interm. 5). In a similar manner, but starting from intermediate (9), was also prepared: (+)-ethyl cis-4-amino-3-methoxy-1-piperidinecarboxylate (interm. 6).

EXAMPLE 4 a) A mixture of 53.3 g of ethyl 3-methoxy-4-oxo-1-piperidinecarboxylate (described in EP-patent 76.350), 33 g of (-)-(R)-α-aminobenzeneethanol and 700 ml of ethanol was refluxed overnight. After cooling, the reaction mixture was evaporated and the residue was distilled, yielding 59.1 g (92%) of ethyl (R)-4-[(2-hydroxy-1-phenylethyl)imino]-3-methoxy-1-piperidinecarboxylate; bp. 180° C. (pressure= 3.75.10$^{-4}$ Pa) (interm. 10).

b) A solution of 59.1 g of intermediate (10) in 500 ml of ethanol was hydrogenated at normal pressure and at room temperature with 2 g of platinum-on-charcoal catalyst. After the calculated amount of hydrogen was taken up, the catalyst was filtered off and the filtrate was evaporated. The residue was purified over $NH_2$-silicagel (eluent $CH_2Cl_2$/cyclohexane/methanol 60:40:0.5). The pure fractions were collected and the eluent was evaporated, yielding 18 g (30%) of ethyl (-)-[4(R),cis]-4-[(2-hydroxy-1-phenylethyl)amino]-3-methoxy-1-piperidinecarboxylate as a residue; $[\alpha]_{20}^D = -96.70°$ (c=0.5% in methanol) (interm. 11).

c) A solution of 18 g of intermediate (11) in 250 ml of methanol was hydrogenated at normal pressure and at room temperature with 2 g of paladium-on-charcoal catalyst 10%. After the calculated amount of hydrogen was taken up, the catalyst was filtered off and the filtrate was evaporated. The resiude was distilled, yielding 6.2 g (55%) of ethyl (-)-cis-4-amino-3-methoxy-1-piperidinecarboxylate (interm. 5).

EXAMPLE 5 a) 4-amino-5-chloro-2,3-dihydro-2,2-dimethyl-7-benzofurancarboxylic acid (described in EP-0,389,037) (0.05 mol) was dissolved in a mixture of N,N-diethylethanamine (7 ml) and trichloromethane (250 ml). Ethyl carbonochloridate (0.05 mol) was added dropwise at <10° C. The reaction mixture was stirred for 30 min at <10° C. The mixture was added to a solution of intermediate (5) (0.047 mol) in trichloromethane (250 ml), stirred at 10° C. The reaction mixture was stirred for 30 min at room temperature. The reaction mixture was washed with water, 5% NaOH and again water. The organic layer was separated, dried ($MgSO_4$), filtered and the solvent was evaporated. The residue was purified by column chromatography over silica gel (eluent: $CH_2Cl_2$/$CH_3OH$ 98/2). The pure fractions were collected and the solvent was evaporated, yielding 19 g (94%) of (+)-ethyl cis-4-[(4-amino-5-chloro-2,3-dihydro-2,2-dimethyl-7-benzofuranyl)-carbonylamino]-3-methoxy-1-piperidinecarboxylate (interm. 12).

b) A mixture of intermediate (12) (0.045 mol) and potassium hydroxide (0.45 mol) in 2-propanol (300 ml) was stirred and refluxed for 12 hours. The reaction mixture was cooled and the solvent was evaporated. Water (100 ml) was added to the residue. The solvent was evaporated. The residue was partitioned between dichloromethane and water. The organic layer was separated, washed with water, dried ($MgSO_4$), filtered and the solvent was evaporated. The residue was purified by column chromatography over silica gel (eluent: $CH_2Cl_2$/($CH_3OH$/$NH_3$) 97/3). The pure fractions were collected and the solvent was evaporated. The residue was dried (vacuum;50° C.), yielding: 12.5 g (+)-cis-4-amino-5-chloro-2,3-dihydro-N-(3-methoxy-4-piperidinyl)-2,2-dimethyl-7-benzofurancarboxamide (77.2%); $[\alpha]_{20}^{365} = 33.40°$ (c=0.5% in methanol) (interm. 13).

EXAMPLE 6 a) A mixture of intermediate (13) (0.017 mol), ethyl (2-chloroethyl)carbamate (0.02 mol) and N,N- diethylethanamine (0.022 mol) in N,N-dimethylformamide (150 ml) was stirred for 72 h at 70° C. The reaction mixture was cooled and the solvent was evaporated. The residue was partitioned between dichloromethane and water. The organic layer was separated, dried (MgSO$_4$), filtered and the solvent was evaporated. The residue was purified over silica gel on a glass filter (eluent: CH$_2$Cl$_2$/CH$_3$OH 97/3). The pure fractions were collected and the solvent was evaporated, yielding: 5 g (+)-ethyl cis-[2-[4-[[(4-amino-5-chloro-2,3-dihydro-2,2-dimethyl-7-benzofuranyl)carbonyl]-amino]-3-methoxy-1-piperidinyl]ethyl]carbamate (63%); $[\alpha]_{20}^{D}$ = 1.20° (c=0.5% in methanol) (interm. 14).

b) A mixture of intermediate (14) (0.0106 mol) and potassium hydroxide (0.106 mol) in 2-propanol (45 ml) was stirred and refluxed for 4 hours. The mixture was cooled. The solvent was evaporated and the residue was stirred in water, then evaporated again. The residue was dissolved in dichloromethane and this solution was washed with a small volume of water, dried (MgSO$_4$), filtered and the solvent was evaporated. The residue was purified over silica gel on a glass filter (eluent: CH$_2$Cl$_2$/CH$_3$OH/(CH$_3$OH/NH$_3$) 90/9/1). The pure fractions were collected and the solvent was evaporated, yielding 3.2 g (76%) (-)-cis-4-amino-N-[1-(2-aminoethyl)-3-methoxy-4-piperidinyl]-5-chloro-2,3-dihydro-2,2-dimethyl-7-benzofurancarboxamide; $[\alpha]_{20}^{D}$ = -1.50° (c=0.2% in methanol) (interm. 15).

EXAMPLE 7 a) A mixture of intermediate (13) (0.023 mol) and 2-propenenittile (0.028 mol) in 2-propanol (150 ml) was stirred and refluxed for 16 hours. The reaction mixture was cooled and the solvent was evaporated, yielding 8 g (85.5%) (-)-cis-4-amino-5-chloro-N-[1-(2-cyanoethyl)-3-methoxy-4-piperidinyl]-2,3-dihydro-2,2-dimethyl-7-benzofurancarboxamide; $[\alpha]_{20}^{D}$=1.60° (c=0.5% in methanol) (interm. 16).

b) A mixture of intermediate (16) (0.02 mol) in methanol (250 ml) and tetrahydrofuran (100 ml) was hydrogenated under atmospheric conditions with Raney nickel (3 g) as a catalyst. After uptake of hydrogen (2 equiv), the catalyst was filtered off and the filtrate was evaporated, yielding 7 g (85.2%) (-)-cis-4-amino-N-[1-(3-aminopropyl)-3-methoxy4-piperidinyl]-5-chloro-2,3-dihydro-2,2-dimethyl-7-benzofurancarboxamide interm. 17).

EXAMPLE 8 a) Intermediate (17) (0.769 mol) was dissolved in 1-butanol (2310 ml) (heating to 50° C. required). Potassium carbonate (1.538 mol) was added at 30° C. (heterogeneous). 2-Chloro-4-methoxypyrimidine (0.960 mol) was added and the reaction mixture was heated to reflux temperature (104° C.). The reaction mixture was stirred and refluxed for 11 hours. The mixture was allowed to cool to 20° C. Water (769 ml) was added and the mixture was stirred for 15 minutes. The layers were separated. The organic layer was evaporated (1.66 mm Hg; 60° C.), yielding 458.9 g (92.1%) of (±)-cis-4-amino-5-chloro-2,3-dihydro-N-[3-methoxy-1-[3-[(4-methoxy-2-pyrimidinyl)amino]propyl]-4-piperidinyl]-2,2-dimethyl-7-benzofurancarboxamide (interm. 18).

b) Hydrochloric acid in 2-propanol (434 ml) was added dropwise over a 15-minutes period to a solution of intermediate (18) (0.769 mol) in 4-methyl-2-pentanone (3845 ml), stirred at 15°–20° C. (cooling on ice bath was required). The reaction mixture was stirred for 1 hour at 15° C. The precipitate was filtered off, washed with 4-methyl-2-pentanone (769 ml) and dried (vacuum; 50° C.), yielding 425.9 g (93.6%) of (±)-cis-4-amino-5-chloro-2,3-dihydro-N-[3-methoxy-1-[3-[(4-methoxy-2-pyrimidinyl)amino]-propyl]-4piperidinyl]-2,2-dimethyl-7-benzofurancarboxamide dihydrochloride (interm. 19)

B. Preparation of the final compounds

EXAMPLE 9

A mixture of intermediate (17) (0.017 mol) and 2-methylthio-4-pyrimidinone (0.022 mol) in acetonitrile (300 ml) was stirred and refluxed for 16 hours. Extra 2-methylthio-4-pyrimidinone (2 g) was added and the reaction mixture was stirred and refluxed for 16 hours. The reaction mixture was cooled. The solvent was evaporated. The residue was purified over silica gel on a glass filter (eluent: CH$_2$Cl$_2$/CH$_3$OH/(CH$_3$OH/NH$_3$) 90/9/1). The pure fractions were collected and the solvent was evaporated. The residue was triturated in 2,2'-oxybispropane. The solid was filtered off and dried (vacuum; room temperature), yielding 2.65 g (29.7%) (-)-cis-4-amino-5-chloro-2,3-dihydro-N-[1-[3-[(3,4-dihydro-4-oxo-2-pyrimidinyl)amino]propyl]-3-methoxy-4-piperidinyl]-2,2-dimethyl-7-benzofurancarboxamide; mp. 164.3° C.; $[\alpha]_{20}^{D}$=-17.54° (c=1% in methanol) (comp. 1).

In this manner there were prepared:

TABLE 1

| Co. No. | R$^3$ | R$^4$ | n | m | physical data |
|---|---|---|---|---|---|
| 1 | OCH$_3$ | NH$_2$ | 3 | 1 | cis; mp. 164.3° C.; $[\alpha]_{20}^{D}$ = -17.54° (c = 1% in methanol) |
| 2 | OCH$_3$ | NH$_2$ | 2 | 1 | cis; mp. 179.9° C., $[\alpha]_{20}^{365}$ = -156.45° (c = 0.1% in CH$_3$OH) |
| 3 | OCH$_3$ | NH$_2$ | 3 | 1 | cis; mp. 164.3° C., $[\alpha]_{20}^{D}$ = 17.21° (c = 1% in CH$_3$OH) |
| 4 | OCH$_3$ | NH$_2$ | 2 | 1 | cis; $[\alpha]_{20}^{365}$ = 158.53° (c = 0.1% in CH$_3$OH) |
| 5 | OCH$_3$ | NH$_2$ | 3 | 1 | cis; 2.5 H$_2$O/mp. 163.8° C. |
| 6 | OCH$_3$ | NH$_2$ | 2 | 1 | cis; mp. 198.8° C. |
| 7 | H | NH$_2$ | 2 | 1 | mp. 204.4° C. |
| 8 | H | NH$_2$ | 3 | 1 | H$_2$O/mp. 165.8° C. |
| 9 | H | NH$_2$ | 3 | 2 | mp. 221.1° C. |
| 10 | H | H | 2 | 1 | mp. 126.9° C. |
| 11 | H | H | 3 | 2 | mp. 106.1° C. |

EXAMPLE 10

A mixture of 4.15 g of 2-chloro-4-hydroxyquinazoline, 4.57 g of 4-amino-N-[1-(3-aminopropyl)-4-piperidinyl]-5-chloro-2,3-dihydro-2,2-dimethyl-7-benzofurancarboxamide (described in EP-0, 445, 862) and 0.80 g of calcium oxide was stirred for 1 hour at 140° C. The reaction mixture was dissolved in a mixture of dichloromethane and methanol. The whole was washed with water, dried, filtered and evaporated. The residue was purified twice by column chromatography (silica gel; $CH_2Cl_2/CH_3OH(NH_3)$ 90:10; $CH_2Cl_2/CH_3OH(NH_3)$ 88:12 ). The eluent of the desired on was evaporated and the residue was boiled in 2,2'-oxybispropane. The product was filtered off and dried, yielding 3.2 g (50.8%) of 4-amino-5-chloro-2,3-dihydro-N-[1-[3-[(4-hydroxy-2-quinazolinyl)amino]propyl]-4-piperidinyl]-2,2-dimethyl-7-benzofurancarboxamide; mp. 159.6° C. (comp. 12).

In this manner there were prepared:

dimethylacetamide was stirred for 3 hours at 140° C. After cooling, the reaction mixture was evaporated and the residue was taken up in a mixture of dichloromethane and methanol. The whole was washed with water. The partly precipitated product was filtered off (first fraction). The organic layer was decanted, dried, filtered and evaporated (second fraction). The combined fractions were purified twice by column chromatography (silica gel; $CH_2Cl_2/CH_3OH(NH_3)$ 95:5; $CH_2Cl_2/CH_3OH$ 92:8). The eluent of the desired fraction was evaporated and the residue was crystallized from aceto-

TABLE 2

| Co. No. | $R^3$ | $R^4$ | n | physical data |
|---|---|---|---|---|
| 12 | H | $NH_2$ | 3 | mp. 159.6° C. |
| 13 | H | $NH_2$ | 4 | mp. 152.3° C. |
| 14 | H | $NH_2$ | 2 | mp. 160° C. (decomp.) |
| 15 | $OCH_3$ | $NH_2$ | 3 | cis/½ $H_2O$/mp. 185.6° C. |
| 16 | $OCH_3$ | $-NH-CO-CH_3$ | 3 | cis; $H_2O$/mp. 181.2° C. |
| 17 | $OCH_3$ | H | 3 | cis; mp. 140.5° C. |
| 18 | $OCH_3$ | H | 2 | cis; mp. 150.0° C. |
| 19 | H | H | 2 | mp. 238.1° C. |
| 20 | H | H | 3 | mp. 131.1° C. |

EXAMPLE 11

A mixture of 2.6 g of 2,6-dichloro-4-quinazolinol (described in J.Med.Chem., 1968, p.130), 3.7 g of 4-amino-N-[1-(2-aminoethyl)-4-piperidinyl]-5-chloro-2,3-dihydro-2,2-dimethyl-7-benzofurancarboxamide (described in EP-0, 445, 862), 0.8 g of calcium oxide and 5.64 g of N,N- nitrile. At 0° C., the product was filtered off and dried in vacuo at 60° C., yielding 1 g (18.3%) of 4-amino-5-chloro-N-[1-[2-[(6-chloro-4-hydroxy-2-quinazolinyl)amino]ethyl]-4-piperidinyl]-2,3-dihydro-2,2-dimethyl-7-benzofurancarboxamide; mp. 206.6° C. (comp. 21).

In this manner there were prepared:

TABLE 3

| Co. No. | $R^1, R^2$ | $R^3$ | n | physical data |
|---|---|---|---|---|
| 21 | $-CH=CH-C(Cl)=CH-$ | H | 2 | mp. 206.6° C. |
| 22 | $-CH=C(Cl)-CH=CH-$ | H | 2 | mp. 242.4° C. |
| 23 | $-CH=C(Cl)-CH=CH-$ | $OCH_3$ | 3 | mp. 215.5° C.; cis |
| 24 | $-CH=CH-C(Cl)=CH-$ | $OCH_3$ | 3 | ½ $H_2O$/mp. 237.9° C.; cis |

EXAMPLE 12

Water (2880 ml) was added to intermediate (19) (0.72 mol, resulting in complete dissolution of intermediate (19). Hydrochloric acid (193 ml) was added dropwise. The reaction mixture was heated to reflux temperature (95° C). The reaction mixture was stirred and refluxed for 24 hours. More hydrochloric acid (128.6 ml) was added at reflux temperature. The reaction mixture was stirred and refluxed for 2.5 hours. Heating was stopped. Dichloromethane (360 ml) was added. The layers were separated. Dichloromethane (1080 ml) was added to the aqueous phase. At 20°–25° C., the biphasic mixture was alkalized with ammonium hydroxide (433 ml) (until pH>10; addition over a 30-minutes period; external cooling required!; the mixture was homogeneous at start, precipitation resulted at pH=6–7 and dissolved at higher pH). The layers were separated. The aqueous layer was extracted with dichloromethane (360 ml). The organic extracts were combined, dried, filtered and evaporated (vacuum; 40° C.). The residue was dried (vacuum; 40° C.), yielding 321.2 g (88.3%) of (-)-cis-4-amino-5-chloro-N-[1-[3-[(3,4-dihydro-4-oxo-2-pyrimidinyl)amino]propyl]-3-methoxy-4-piperidinyl]-2,3-dihydro-2,2-dimethyl-7-benzofurancarboxamide (comp. 1).

C. Pharmacological example

EXAMPLE 13 von Bezold Jarish test

Male spontaneous hypertensive rats (±6 months) were anaesthetized by ether inhalation and the femoral vein and artery were dissected and cannulated with polyethylene catheters. Lidocaine (20%) was administered to the wound around the cannulas to induce local analgesia.

The animals were restrained in Bollman cages, and the arterial catheter was connected to a strain guage blood pressure transducer and systolic pressure was analysed. When the animals were fully awake a control injection of serotonin (0.04 mg/kg) was given via the femoral vein catheter. The response of the systolic blood pressure to a intravenous serotine injection normally evolves in three phases: 1) a short and sharp decrease (von Bezold-Jarish reflex), 2) an increase and 3) a longer lasting decrease in systolic blood pressure. Inhibition of the first sharp decrease in blood pressure (von Bezold-Jarish reflex) is taken as a measure for 5-$HT_3$-antagonism. Some time after the control injection of serotonin the test compound was injected intraperitoneally. After 30 minutes serotonin was again injected intravenously and the presence or absence of the first short and sharp decrease was recorded. The same procedure was repeated after 60 minutes. The compounds were tested at different doses.

The Lowest Active Dose (LAD) which is shown in Table 4 may be defined as the dose (in mg/kg body weight) at which at least half of the animals tested show inhibition of the von Bezold-Jarish reflex.

TABLE 4

| Co. No. | LAD (mg/kg) |
| --- | --- |
| 5 | 0.04 |
| 7 | 0.04 |
| 9 | 0.16 |
| 12 | 0.16 |
| 14 | 0.01 |
| 19 | 0.01 |

TABLE 4-continued

| Co. No. | LAD (mg/kg) |
| --- | --- |
| 21 | 0.16 |
| 11 | 0.16 |
| 8 | 0.04 |
| 24 | 0.16 |
| 23 | 0.16 |
| 16 | 0.16 |
| 17 | 0.04 |
| 6 | 0.01 |
| 10 | 0.01 |
| 1 | 0.04 |
| 2 | 0.04 |

D. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid addition salt or a stereochemically isomeric form thereof.

EXAMPLE 14

Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE 15

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I..

EXAMPLE 16

Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

We claim:

1. A method of treating 5-$HT_3$-mediated disorders which comprises administering to subjects suffering from 5-$HT_3$-mediated disorders an effective amount of a compound of the formula:

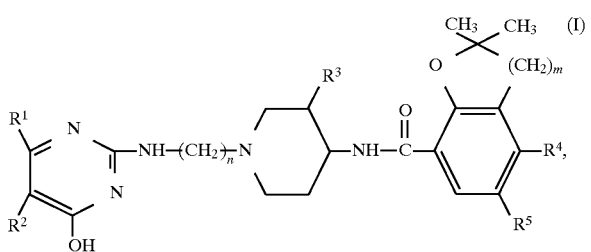

a pharmaceutically acceptable acid addition salt form or a stereochemically isomeric form thereof, wherein:

$R^1$ and $R^2$ represent hydrogen;

n represents 2, 3 or 4;

$R^3$ represents hydrogen or methoxy;

m represents 1 or 2;

$R^4$ represents hydrogen, amino or $C_{1-3}$alkylcarbonylamino; and

R represents hydrogen or halo.

2. A method according to claim 1, wherein $R^3$ represents methoxy and has the cis-configuration.

3. A method according to claim 2, wherein the compound is laevo-rotatory.

4. A method according to claim 1, wherein the compound is (-)-cis-4-amino-5-chloro-2,3-dihydro-N-[1-[3-[(3,4-dihydro-4-oxo-2-pyrimidinyl)amino]propyl]-3-methoxy-4-piperidinyl]-2,2-dimethyl-7-benzofurancarboxamide or (-)-cis-4-amino-5-chloro-N-[1-[2-[(3,4-dihydro-4-oxo-2-pyrimidinyl)amino]ethyl]-2,3-dihydro-3-methoxy-4-piperidinyl]-2,2-dimethyl-7-benzofurancarboxamide, or a pharmaceutically acceptable acid addition salt form thereof.

5. The method of claim 1, wherein the 5-$HT_3$ mediated disorder is selected from the group consisting of anxiety, psychosis, depression, schizophrenia, cognitive disorders, drug abuse, migraine, emesis and irritable bowel syndrome.

6. The method of claim 2, wherein the 5-$HT_3$ mediated disorder is selected from the group consisting of anxiety, psychosis, depression, schizophrenia, cognitive disorders, drug abuse, migraine, emesis and irritable bowel syndrome.

7. The method of claim 3, wherein the 5-$HT_3$ mediated disorder is selected from the group consisting of anxiety, psychosis, depression, schizophrenia, cognitive disorders, drug abuse, migraine, emesis and irritable bowel syndrome.

8. The method of claim 4, wherein the 5-$HT_3$ mediated disorder is selected from the group consisting of anxiety, psychosis, depression, schizophrenia, cognitive disorders, drug abuse, migraine, emesis and irritable bowel syndrome.

* * * * *